(12) United States Patent
Vardhan et al.

(10) Patent No.: US 10,981,858 B2
(45) Date of Patent: Apr. 20, 2021

(54) DENDRIMER AND FORMULATIONS THEREOF

(71) Applicants: Priostar Pty Ltd, Abbotsford (AU); Dendritic Nanotechnologies, Inc., Loveland, CO (US)

(72) Inventors: Harsh Vardhan, Abbotsford (AU); Sarigama Rajesh, Abbotsford (AU); Peter Karellas, Abbotsford (AU)

(73) Assignees: Priostar Pty Ltd, Victoria (AU); Dendritic Nanotechnologies, Inc., Loveland, CO (US)

( * ) Notice: Subject to any disclaimer, the term of this patent is extended or adjusted under 35 U.S.C. 154(b) by 205 days.

(21) Appl. No.: 16/062,087

(22) PCT Filed: Dec. 16, 2016

(86) PCT No.: PCT/AU2016/051246
§ 371 (c)(1),
(2) Date: Jun. 13, 2018

(87) PCT Pub. No.: WO2017/100856
PCT Pub. Date: Jun. 22, 2017

(65) Prior Publication Data
US 2018/0370900 A1    Dec. 27, 2018

(30) Foreign Application Priority Data

Dec. 16, 2015 (AU) ................. 2015905221

(51) Int. Cl.
| | |
|---|---|
| A01N 33/08 | (2006.01) |
| C07C 217/40 | (2006.01) |
| A01N 25/04 | (2006.01) |
| A01N 25/30 | (2006.01) |
| C07C 217/28 | (2006.01) |
| A01N 25/02 | (2006.01) |

(52) U.S. Cl.
CPC ............ *C07C 217/40* (2013.01); *A01N 25/02* (2013.01); *A01N 25/04* (2013.01); *A01N 25/30* (2013.01); *A01N 33/08* (2013.01); *C07C 217/28* (2013.01); *A01N 2300/00* (2013.01)

(58) Field of Classification Search
None
See application file for complete search history.

(56) References Cited

U.S. PATENT DOCUMENTS

| | | | |
|---|---|---|---|
| 6,939,831 | B1 | 9/2005 | Caminade et al. |
| 7,981,444 | B2 | 7/2011 | Tomalia et al. |
| 7,985,424 | B2 | 7/2011 | Tomalia et al. |
| 9,585,387 | B1 | 3/2017 | Hayes et al. |
| 2001/0041170 | A1 | 11/2001 | Winchell et al. |
| 2007/0244296 | A1 | 10/2007 | Tomalia et al. |
| 2012/0024789 | A1 | 2/2012 | Sarkar et al. |
| 2012/0053057 | A1 | 3/2012 | Cristadoro et al. |

FOREIGN PATENT DOCUMENTS

| | | |
|---|---|---|
| CN | 1343091 A | 4/2002 |
| CN | 1946772 A | 4/2007 |
| CN | 102781231 A | 11/2012 |
| EP | 3390348 | 10/2018 |
| WO | 2006/065266 A2 | 6/2006 |
| WO | 2007/149500 A2 | 12/2007 |
| WO | 2010/132097 A2 | 11/2010 |
| WO | 2011/009652 A2 | 1/2011 |
| WO | WO 2011/019652 A2 | 2/2011 |
| WO | WO 2011/053605 A1 | 5/2011 |
| WO | 2017/100856 A1 | 6/2017 |

OTHER PUBLICATIONS

International Search Report and Written Opinion issued by the Australian Patent Office, dated Mar. 6, 2017, for International Application No. PCT/AU2016/051246; 8 pages.
Baig, T.; et al. (2015). A review about dendrimers: synthesis, types, characterization and applications. International Journal of Advances in Pharmacy, Biology and Chemistry, 4(1):44-59.
EP Examination Report issued in EP Application No. 16874147.8, dated Aug. 4, 2020, 5 pages.
Extended European Search Report issued in EP Application No. 16874147.8, dated Apr. 2, 2019, 11 pages.
Fernandez, L.; et al. (2011). Solubility improvement of an anthelmintic benzimidazole carbamate by association with dendrimers. Brazilian Journal of Chemical Engineering, 28(04):679-689.
Intellectual Property India Patent Office First Examination Report on Patent Application No. 201817026316, issued Mar. 11, 2020, 6 pages.
International Preliminary Report on Patentability issued in PCT/AU2016/051246, dated Jun. 19, 2018, 5 pages.
Klajnert, B., and Bryszewska, M. (2001). Dendrimers: properties and applications. Acta Biochimica Polonica, 48 (Jan. 2001):199-208.

*Primary Examiner* — Erin E Hirt
(74) *Attorney, Agent, or Firm* — Faegre Drinker Biddle & Reath LLP

(57) ABSTRACT

The present invention relates to a novel dendrimer. The present invention also relates to formulations comprising the dendrimer with improved characteristics. For instance, the present invention relates to formulations comprising pesticides such as 2-(2,4-dichlorophenoxy)acetic acid with improved characteristics such as reduced crystallisation, compatibility with hard water and an extended shelf life at low temperatures.

20 Claims, No Drawings

DENDRIMER AND FORMULATIONS THEREOF

CROSS-REFERENCE TO RELATED APPLICATIONS

This application is a U.S. National Stage Application of International Patent Application No. PCT/AU2016/051246, filed Dec. 16, 2016, which claims the benefit of Australian Provisional Patent Application No. 2015905221, filed Dec. 16, 2015, the complete disclosures each of which is expressly incorporated herein by reference in its entirety.

FIELD

The present invention relates to a novel dendrimer. The present invention also relates to formulations comprising the dendrimer with improved characteristics. For instance, the present invention relates to formulations comprising pesticides such as soluble liquid formulations with improved stability characteristics.

BACKGROUND

The occurrence of pests is a constant problem facing farmers in crops, pastures, and other settings. For instance, weeds compete with crops and negatively impact crop yield, whereas some insect species eat crops and others negatively impact animal health. The use of chemical pesticides is an important tool in controlling undesirable species such as plants and insects. In an effort to overcome this issue, researchers have developed multiple lines of attack, including the production of new synthetic compounds, and combining these with either known or novel pesticides to yield new formulations that display a high efficacy in the eradication of unwanted plants and insects.

Dendrimers are highly branched, often spherical molecules, in which terminal branches can be tailored to include an array of functional groups, for example charged amino groups. These groups can be adapted for specific applications. Due to their controlled chemical synthesis, dendrimers have a very precise size and defined shape.

There is a need for the identification of novel dendrimers which have desirable enhanced characteristics. Furthermore, there remains a need for chemical compositions for controlling pests with improved properties.

SUMMARY

The present inventors have identified a novel dendrimer which has a number of useful characteristics.

Thus, in a first aspect the present invention provides a dendrimer having the structure of Compound 4:

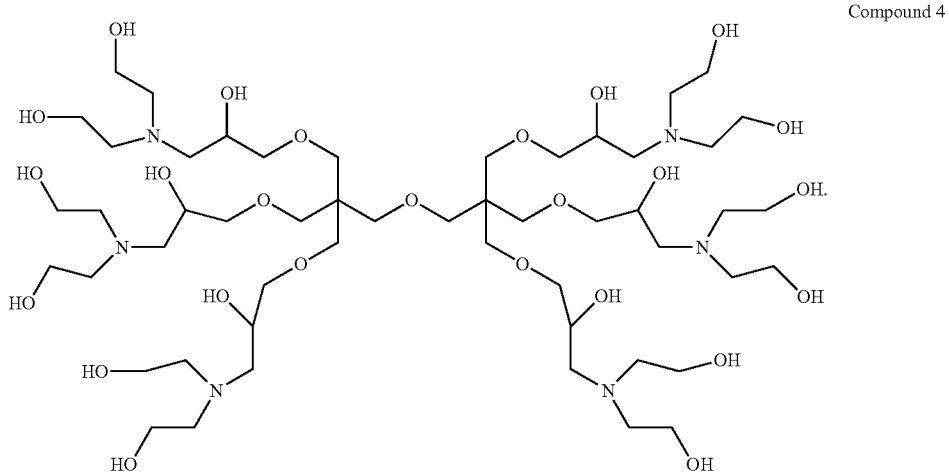 [SMILES: OCCN(CCO)CC(O)COCC(COCC(O)CN(CCO)CCO)(COCC(O)CN(CCO)CCO)COCC(COCC(O)CN(CCO)CCO)(COCC(O)CN(CCO)CCO)COCC(O)CN(CCO)CCO]

Compound 4

9,9'-(Oxybis(methylene))bis(9-((3-(bis(2-hydroxy-ethyl)amino)-2-hydroxypropoxy) methyl)-3,15-bis (2-hydroxyethyl)-7,11-dioxa-3,15-diazaheptadecane-1,5,13,17-tetraol) (hereinafter "Compound 4").

In one aspect the present invention provides a composition comprising a dendrimer having the structure of Compound 4 and one or more acceptable excipients or carriers.

In another aspect, the present invention provides a composition comprising a mixture of dendrimers of Formula 1:

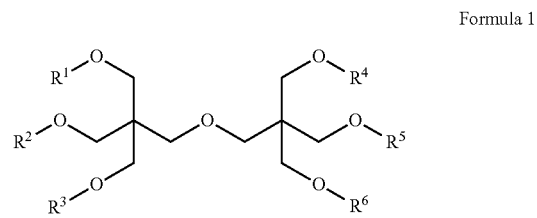

Formula 1 wherein each of $R^1$, $R^2$, $R^3$, $R^4$, $R^5$ and $R^6$ are independently selected from:

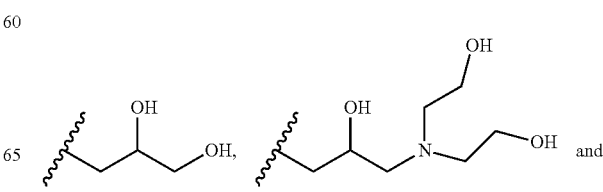

-continued

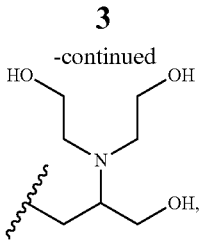

with the proviso that Compound 4 is present in the mixture of dendrimers.

In another aspect the present invention provides a formulation comprising a mixture of dendrimers of Formula 1:

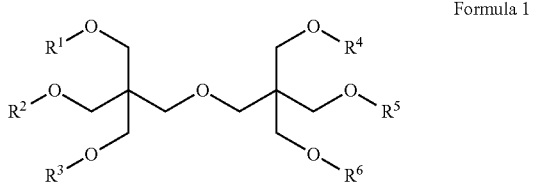

Formula 1 wherein each of $R^1$, $R^2$, $R^3$, $R^4$, $R^5$ and $R^6$ are independently selected from:

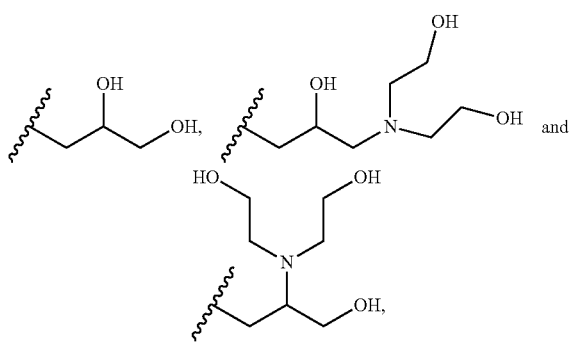

with the proviso that Compound 4 is present in the mixture of dendrimers, and one or more acceptable carriers.

In one embodiment Compound 4 is present in the mixture of dendrimers in an amount of: at least about 30% (w/w), or at least about 40%, or at least about 50% (w/w), or at least about 60% (w/w), or at least about 70% (w/w), or at least about 80% (w/w), or at least about 90% (w/w), or at least about 95% (w/w).

In another aspect, the present invention provides a formulation comprising Compound 4 and one or more acceptable carriers.

In an embodiment, the formulation further comprises a pesticide such as a herbicide, fungicide or an insecticide. Examples of pesticides which can be used in a formulation of the invention include, but are not limited to, a phenoxy herbicide, a dichloro-benzoic acid herbicide, a trichloro-benzoic acid herbicide, an imidazolinone herbicide, a neonicotinoid insecticide and an organophosphate insecticide.

In an embodiment, the pesticide is selected from: a phenoxy herbicide, a dichloro-benzoic acid herbicide and a trichloro-benzoic acid herbicide.

In another embodiment, the phenoxy herbicide is a mono or di chlorophenoxy herbicide or a phenoxyacetic herbicide. In a further embodiment, the phenoxy herbicide is a phenoxyacetic herbicide.

Examples of phenoxyacetic herbicides which can be used in a formulation of the invention include, but are not limited to, 2-(2,4-dichlorophenoxy)acetic acid (2,4-D), 2-(4-chlorophenoxy) acetic acid, 1-(dimethoxyphosphinyl)ethyl 2-(2,4-dichlorophenoxy) acetate, 2-(3,4-dichlorophenoxy)acetic acid, 2-(4-chloro-2-methylphenoxy) acetic acid, S-ethyl 2-(4-chloro-2-methylphenoxy)ethanethioate and 2-(2,4,5-trichlorophenoxy) acetic acid, or salts and esters thereof.

In a preferred embodiment, the phenoxyacetic herbicide is 2-(2,4-dichlorophenoxy) acetic acid (2,4-D) or a salt or ester thereof. In an embodiment, the 2,4-D salt or ester is an amine salt or ester.

Examples of dichloro-benzoic acid herbicides or trichloro-benzoic acid herbicides which can be used in a formulation of the invention include, but are not limited to, (phenylimino)di-2,1-ethanediyl bis(3,6-dichloro-2-methoxybenzoate), 3-amino-2,5-dichlorobenzoic acid, 3,6-dichloro-2-methoxybenzoic acid, 2,3,6-trichlorobenzoic acid and 2,3,5-trichloro-6-methoxybenzoic acid, or salts and esters thereof.

In an embodiment, the formulation is a concentrated formulation. In a further embodiment the formulation is a soluble liquid.

Examples of the acceptable carrier which may be present in a formulation include, but are not limited to, water, or primary, secondary or tertiary alcohols. The formulation may be an aqueous solution. The formulation may be a concentrate formulation. The formulation may be an aqueous concentrate solution. The formulation may be a suspension concentrate (SC), soluble concentrate (SL), oil in water emulsion (EW), or emulsifiable concentrate (EC).

In an embodiment, the formulation of the invention further comprises a surfactant. Any suitable surfactant can be used such as a non-ionic, anionic or cationic surfactant. In an embodiment, the surfactant is an amine based surfactant.

In an embodiment, the dendrimer is at a concentration of at least about 5%, at least about 8% or about least 10% (w/w). In a further embodiment, the dendrimer is at a concentration of between about 5% and about 20% (w/w) or at a concentration of between about 2% to about 10% (w/w), or at a concentration of between about 6% to about 10% (w/w).

In an embodiment, the formulation, which may be a concentrated formulation or a soluble liquid formulation, has increased formulation stability, preferably one or more or all of reduced crystallisation or reduced hard water incompatibility or increased shelf life, when compared to a formulation comprising the same components but lacking the dendrimer and/or when compared a formulation where the dendrimer has been replaced with
  (i) other first generation hydroxy terminal group dendrimers such as 9-((3-(bis (2-hydroxyethyl)amino)-2-hydroxypropoxy)methyl)-9-ethyl-3,15-bis (2-hydroxyethyl)-7,11-dioxa-3,15-diazaheptadecane-1,5,13,17-tetraol (Compound 1), described in WO06/065266 and WO11/053605; or
  (ii) other G1 PETGE core dendrimers, such as:
    (a) morpholine terminal groups, such as 3,3'-((2-ethyl-2-((2-hydroxy-3-morpholinopropoxy) methyl)propane-1,3-diyl) bis(oxy))bis(1-morpholinopropan-2-ol (compound 3), described in WO06/115547, Example 65; or
    (b) methoxy terminal group dendrimers, such as (11-((3-(bis(2-methoxyethyl) amino)-2-hydroxypropoxy)methyl)-11-ethyl-5,17-bis (2-methoxyethyl)-2,9,13,20-tetraoxa-5,17-diazahenicosane-7,15-diol (compound 8) described in WO11/053605, Example 15.

In an embodiment, the formulation, which may be a concentrated formulation or a soluble liquid formulation, does not form crystals after storage at 0° C. for seven days.

In another aspect, the present invention provides a method of controlling a pest(s) in an area, the method comprising applying to the area a formulation comprising a dendrimer of Compound 4 having the structure:

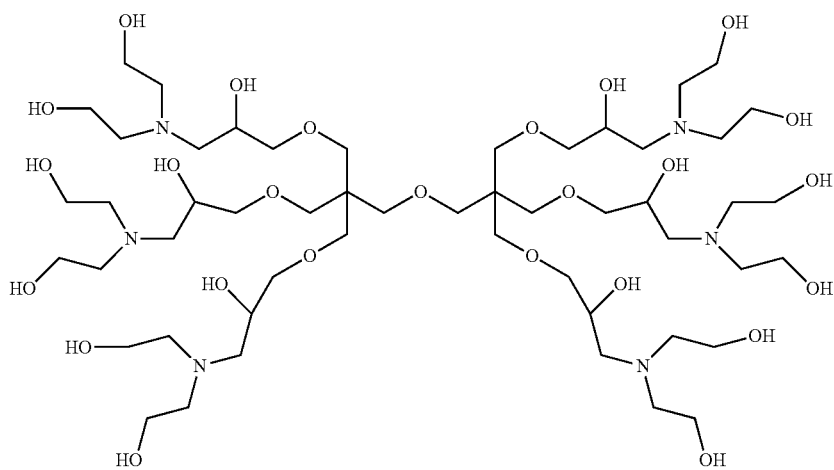

Compound 4 and a pesticide.

In another aspect, the present invention provides use of:
a dendrimer of Compound 4 having the structure:

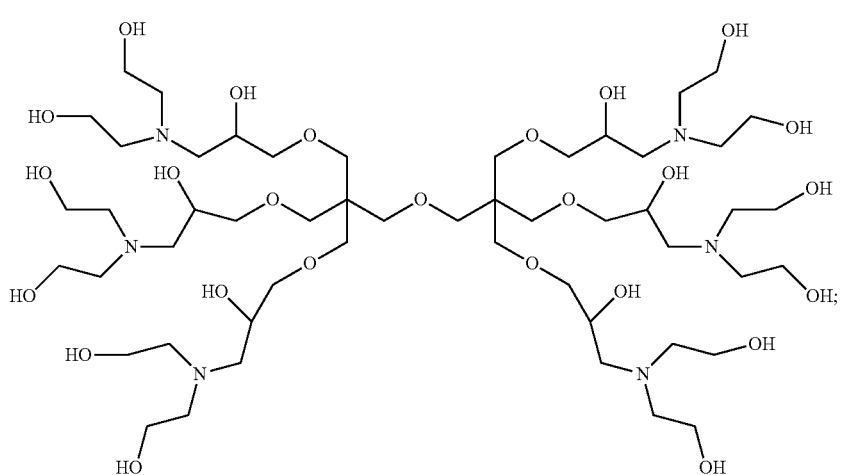

Compound 4 and
a pesticide,
in the production of a formulation for controlling a pest(s) in an area.

In an embodiment, the pest(s) is a weed(s) or an insect(s).

In an embodiment, the pest(s) is a weed(s) and the pesticide is a herbicide.

In an embodiment, the pest(s) is a fungus/fungi and the pesticide is a fungicide.

In an embodiment, the formulation has one or more the features defined above in relation to a formulation of the invention.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

DETAILED DESCRIPTION

General Techniques and Definitions

Unless specifically defined otherwise, all technical and scientific terms used herein shall be taken to have the same meaning as commonly understood by one of ordinary skill in the art (e.g., in agricultural chemistry, dendrimer chemistry, pesticide chemistry and formulations, and biochemistry).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−1%, of the designated value.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial (except where integers are required), numbers within the recited range, for example, 1, 2, 3, 4, 5, 5.5 and 6. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "formulation(s)" means a product comprising specified ingredients in predetermined amounts or proportions, as well as any product that results, directly or indirectly, from combining specified ingredients in specified amounts.

"Formulation stability" as used herein means the propensity of the formulation to degrade, become unstable, separate, precipitate, crystallise, or flocculate.

As used herein, the term "pesticide" or related terms means capable of being toxic to a target pest organism(s) (e.g., weeds, fungus or insect pests), controlling the target pest organism(s), killing the target pest organism(s), inhibiting the growth of the target pest organism(s), and/or inhibiting the reproduction of the target pest organism(s).

As used herein, the term "herbicide" or related terms means capable of being toxic to a plant (e.g., a weeds), controlling a plant, killing a plant, inhibiting the growth of a plant, and/or inhibiting the reproduction of a plant.

As used herein, the term "fungicide" or related terms means capable of being toxic to a fungus, controlling a fungus, killing a fungus, inhibiting the growth of a fungus, and/or inhibiting the reproduction of a fungus.

As used herein, the term "insecticide" or related terms means capable of being toxic to an insect, controlling an insect, killing an insect, inhibiting the growth of an insect, and/or inhibiting the reproduction of an insect.

As used herein, the term "control" or "controlling" as in e.g., the phrase: the "controlling" a pest(s), means preventing, reducing, killing, inhibiting the growth of, inhibiting the reproduction of, and/or eliminating at least one target pest such as a plant (weed) or insect. Indeed, "control" or "controlling" as used herein refers to any indicia of success in prevention, killing, inhibition, elimination, reduction or amelioration of at least one target pest.

As used herein, the term "weed" means any plant targeted for treatment with a formulation of the invention. Target plants can be nuisance, unwanted, noxious, weedy, invasive, or harmful plant or vegetation (e.g., harmful to animals, harmful to ornamental plants, crops, etc.). The term "desirable plant(s)" means any plant that is not a target for such treatment or that may benefit from target weeds being controlled or eliminated.

Formulations of the invention will be used in an effective amount. As used herein, the terms "effective amount", "effective concentration" or "effective dosage" means the amount, concentration, or dosage of at least one active ingredient (e.g., 2,4-D) sufficient for controlling at least target pest organism. The actual effective dosage in absolute value depends on factors including, but not limited to, synergistic or antagonistic interactions between the other active or inert ingredients which may enhance or reduce the controlling effects of the at least one active ingredient and/or the stability of the at least one active ingredient in the formulation. The "effective amount", "effective concentration", or "effective dosage" of the at least one active ingredient may be determined, e.g., by a routine dose response experiment.

Actives

Formulations of the invention will typically comprise one or more active components.

In an embodiment, the active is a pesticide such as a herbicide, fungicide or an insecticide. In an embodiment, the pesticide is selected from: a phenoxy herbicide, a dichloro-benzoic acid herbicide, a trichloro-benzoic acid herbicide, an imidazolinone herbicide, a neonicotinoid insecticide and an organophosphate insecticide.

In one embodiment the pesticide is in the form of a free acid.

In one embodiment the pesticide is in the form of a salt.

In one embodiment the pesticide is in the form of an ester.

In one embodiment, the herbicide is a phenoxy herbicide. Examples of phenoxy herbicides which can be present in a formulation of the invention include, but are not limited to: phenoxyacetic herbicides, phenoxybutyric herbicides, phenoxypropionic herbicides and aryloxyphenoxypropionic herbicides. Other examples of phenoxy herbicides which can be present in a formulation of the invention include, but are not limited to, 3,5-dibromo-4-hydroxybenzaldehyde O-(2,4-dinitrophenyl)oxime, 2-(2,4-dichloro-3-methylphenoxy)-N-phenylpropanamide, 2-(2,4-dichlorophenoxy)ethyl benzoate, tris[2-(2,4-dichlorophenoxy)ethyl] phosphite, (2E)-4-[4-[4-(trifluoromethyl) phenoxy]phenoxy]-2-pentenoic acid, 2-(2,4-dichlorophenoxy)ethyl hydrogen sulfate, 2-(2,4,5-trichlorophenoxy)ethyl 2,2-dichloropropanoate, 2-[5-(2,4-dichlorophenoxy)-2-nitrophenoxy]-N-ethylpropanamide, 2-(2,4,5-trichlorophenoxy) ethanol, and 2-propanone O-[(2R)-1-oxo-2-[4-[4-(trifluoromethyl) phenoxy]propyl]oxime, or salts and esters thereof.

In an embodiment, the phenoxy herbicide is a phenoxyacetic herbicide. Examples of phenoxyacetic herbicide which can be present in a formulation of the invention include, but are not limited to, 2-(2,4-dichlorophenoxy) acetic acid (2,4-D), 2-(4-chlorophenoxy) acetic acid, 1-(dimethoxyphosphinyl)ethyl 2-(2,4-dichlorophenoxy) acetate, 2-(3,4-dichlorophenoxy)acetic acid, 2-(4-chloro-2-methylphenoxy) acetic acid, S-ethyl 2-(4-chloro-2-methylphenoxy)ethanethioate and 2-(2,4,5-trichlorophenoxy) acetic acid, or salts and esters thereof. In a preferred embodiment, the phenoxyacetic herbicide is 2-(2,4-dichlorophenoxy)acetic acid (2,4-D), or a salt or ester thereof. In an embodiment, the 2,4-D salt or ester is an amine salt or ester. In one embodiment the pesticide is 2,4-D in the form of a free acid. In one embodiment the pesticide is 2,4-D in the form of a salt. In one embodiment the pesticide is 2,4-D in the form of an ester. Appropriate salts and esters of 2,4-D includes, but is not limited to: choline, dimethylamine, isopropylamine or diethanolamine salts; methyl, ethyl, propyl, butyl, or isooctyl esters; or a mixture of one or more thereof. In one embodiment, the amine salt is dimethylamine salt or diethanolamine salt; or a mixture of both.

Examples of phenoxybutyric herbicides which can be present in a formulation of the invention include, but are not limited to, 4-(4-chlorophenoxy)butanoic acid, 4-(2,4-dichlorophenoxy) butanoic acid, 4-(3,4-dichlorophenoxy)butanoic acid, 4-(4-chloro-2-methylphenoxy) butanoic acid, and 4-(2,4,5-trichlorophenoxy)butanoic acid or salts and esters thereof.

Examples of phenoxypropionic herbicides which can be present in a formulation of the invention include, but are not limited to, 2-(3-chlorophenoxy)propanoic acid, 2-(4-chlorophenoxy) propanoic acid, 2-(2,4-dichlorophenoxy)propanoic acid, (2R)-2-(2,4-dichlorophenoxy) propanoic acid, 2-(3,4-dichlorophenoxy)propanoic acid, 2-(2,4,5-trichlorophenoxy) propanoic acid, 2-(4-chloro-2-methylphenoxy) propanoic acid, and (2R)-2-(4-chloro-2-methylphenoxy) propanoic acid or salts and esters thereof.

Examples of aryloxyphenoxypropionic herbicides which can be present in a formulation of the invention include, but are not limited to, 2-[4-[(3,5-dichloro-2-pyridinyl) oxy]phenoxy]propanoic acid, (2R)-2-[4-[(5-chloro-3-fluoro-2-pyridinyl) oxy]phenoxy]propanoic acid, 2-[4-(4-chlorophenoxy)phenoxy]propanoic acid, (2R)-2-[4-(4-cyano-2-fluorophenoxy)phenoxy]propanoic acid, 2-[4-(2,4-dichlorophenoxy) phenoxy]propanoic acid, 2-[4-[(6-chloro-2-benzoxazolyl) oxy]phenoxy]propanoic acid, (2R)-2-[4-[(6-chloro-2-benzoxazolyl) oxy]phenoxy]propanoic acid, 2-[4-[(6-chloro-2-benzothiazolyl) oxy]phenoxy]propanoic acid, 2-[4-[[5-(trifluoromethyl)-2-pyridinyl]oxy]phenoxy] propanoic acid, (2R)-2-[4-[[5-(trifluoromethyl)-2-pyridinyl] oxy]phenoxy]propanoic acid, 2-[4-[[3-chloro-5-(trifluoromethyl)-2-pyridinyl]oxy]phenoxy]propanoic acid, (2R)-2-[4-[[3-chloro-5-(trifluoromethyl)-2-pyridinyl]oxy]phenoxy] propanoic acid, 2-[2-[4-[(3,5-dichloro-2-pyridinyl) oxy] phenoxy]-1-oxopropyl]isoxazolidine, 1-(ethoxycarbonyl)-2-methyl-2-propen-1-yl 2-[4-[(6-chloro-2-quinoxalinyl) oxy]phenoxy]propanoate, (2R)-2-[4-[(6-chloro-2-benzoxazolyl) oxy]phenoxy]-N-(2-fluorophenyl)-N-methylpropanamide, 2-[[(1-methylethylidene)amino]oxy] ethyl (2R)-2-[4-[(6-chloro-2-quinoxalinyl) oxy]phenoxy] propanoate, 2-[4-[(6-chloro-2-quinoxalinyl) oxy]phenoxy] propanoic acid, (2R)-2-[4-[(6-chloro-2-quinoxalinyl) oxy] phenoxy]propanoic acid, and 2-[4-[4-(trifluoromethyl) phenoxy]phenoxy]propanoic acid, or salts and esters thereof.

Examples of dichloro-benzoic acid herbicides or trichloro-benzoic acid herbicides which can be present in a formulation of the invention include, but are not limited to, (phenylimino)di-2,1-ethanediyl bis(3,6-dichloro-2-methoxybenzoate), 3-amino-2, 5-dichlorobenzoic acid, 3,6-dichloro-2-methoxybenzoic acid, 2,3,6-trichlorobenzoic acid and 2,3,5-trichloro-6-methoxybenzoic acid, or salts and esters thereof.

Examples of imidazolinone herbicides which can be present in a formulation of the invention include, but are not limited to, 2-[4,5-dihydro-4-methyl-4-(1-methylethyl)-5-oxo-1H-imidazol-2-yl]-4 (or 5)-methylbenzoic acid, 2-[4,5-dihydro-4-methyl-4-(1-methylethyl)-5-oxo-1H-imidazol-2-yl]-5-(methoxymethyl)-3-pyridinecarboxylic acid, 2-[4,5-dihydro-4-methyl-4-(1-methylethyl)-5-oxo-1H-imidazol-2-yl]-5-methyl-3-pyridinecarboxylic acid, 2-[4,5-dihydro-4-methyl-4-(1-methylethyl)-5-oxo-1H-imidazol-2-yl]-3-pyridinecarboxylic acid, 2-[4,5-dihydro-4-methyl-4-(1-methylethyl)-5-oxo-1H-imidazol-2-yl]-3-quinolinecarboxylic acid, and 2-[4,5-dihydro-4-methyl-4-(1-methylethyl)-5-oxo-1H-imidazol-2-yl]-5-ethyl-3-pyridinecarboxylic acid, or salts and esters thereof.

Examples of neonicotinoid insecticides which can be present in a formulation of the invention include, but are not limited to, [C(E)]-N-[(2-chloro-5-thiazolyl)methyl]-N'-methyl-N"-nitroguanidine, N-methyl-N'-nitro-N"-[(tetrahydro-3-furanyemethyl]guanidine, (2E)-1-[(6-chloro-3-pyridinyl)methyl]-N-nitro-2-imidazolidinimine, 1-[(2-chloro-5-thiazolyl)methyl]-4,5-dihydro-N-nitro-1H-imidazol-2-amine, 3-[(2-chloro-5-thiazolyl)methyl] tetrahydro-5-methyl-N-nitro-4H-1,3,5-oxadiazin-4-imine, (1E)-N-[(6-chloro-3-pyridinyl)methyl]-N-ethyl-N'-methyl-2-nitro-1,1-ethenediamine, tetrahydro-2-(nitromethylene)-2H-1,3-thiazine, (1E)-N-[(6-chloro-3-pyridinyl) methyl]-N'-cyano-N-methylethanimidamide, (2E)-1-[(6-chloro-3-pyridinyl) methyl]-N-nitro-2-imidazolidinimine, (1E)-N-[(6-chloro-3-pyridinyl)methyl]-N-ethyl-N'-methyl-2-nitro-1, 1-ethenediamine, and 1-[(6-chloro-3-pyridinyl)methyl]-1,2,3,5,6,7hexahydro-7-methyl-8-nitro-5-propoxyimidazo[1,2-a]pyridine, (Z)-[3-[(6-chloro-3-pyridinyl) methyl]-2-thiazolidinylidene]cyanamide, or salts and esters thereof.

Examples of organophosphate insecticides which can be present in a formulation of the invention include, but are not limited to, 2-bromo-1-(2,4-dichlorophenyl) ethenyl diethyl phosphate, 2,2-dichloroethenyl dimethyl phosphate compound with calcium bis(2,2-dichloroethenyl methyl phosphate) (2:1), 2-chloro-1-(2,4-dichlorophenyl) ethenyl diethyl phosphate, 1-phenylethyl (2E)-3-[(dimethoxyphosphinyl) oxy]-2-butenoate, 2,2-dichloroethenyl dimethyl phosphate, (1E)-3-(dimethylamino)-1-methyl-3-oxo-1-propen-1-yl dimethyl phosphate, (1Z)-2-chloro-1-(2,4-dichlorophenyl) ethenyl dimethyl phosphate, dimethyl 3,5,6-trichloro-2-pyridinyl phosphate, 7-chlorobicyclo[3.2.0] hepta-2,6-dien-6-yl dimethyl phosphate, (1E)-3-(methoxymethylamino)-1-methyl-3-oxo-1-propen-1-yl dimethyl phosphate, methyl 3-[(dimethoxyphosphinyl)oxy]-2-butenoate, dimethyl (1E)-1-methyl-3-(methylamino)-3-oxo-1-propen-1-yl phosphate, 1,2-dibromo-2,2-dichloroethyl dimethyl phosphate, 2-[(diethoxyphosphinyl)oxy]-1H-benz[de]isoquinoline-1,3 (2H)-dione, 2-chloro-3-(diethylamino)-1-methyl-3-oxo-1-propen-1-yl dimethyl phosphate, 4-(methylthio) phenyl dipropyl phosphate, tetraethyl diphosphate, and (1Z)-2-chloro-1-(2,4,5-trichlorophenyl) ethenyl dimethyl phosphate, or salts and esters thereof.

In an embodiment the pesticide is a fungicide. The fungicide may be selected from, but not limited to: aliphatic nitrogen fungicides, amide fungicides, antibiotic fungicides, strobilurin fungicides, aromatic fungicides, arsenical fungicides, aryl phenyl ketone fungicides, benzimidazole fungicides, benzimidazole precursor fungicides, benzothiazole fungicides, botanical fungicides, bridged diphenyl fungicides, carbamate fungicides, conazole fungicides, copper fungicides, cyanoacrylate fungicides, dicarboximide fungicides, dinitrophenol fungicides, dithiocarbamate fungicides, dithiolane fungicides, fumigant fungicides, hydrazide fungicides, imidazole fungicides, inorganic fungicides, mercury fungicides, morpholine fungicides, organophosphorus fungicides, organotin fungicides, oxathiin fungicides, oxazole fungicides, polysulfide fungicides, pyrazole fungicides, pyridine fungicides, pyrimidine fungicides, pyrrole fungicides, quinoline fungicides, quinone fungicides, quinoxaline fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, and zinc fungicides. In another embodiment the fungicide is a copper salt.

As used herein, salts and esters refer to salts and esters that exhibit pesticidal, such as herbicidal, fungicidal or insecticidal, activity or that are or can be converted in plants, water, or soil to the referenced pesticide.

Examples of suitable acceptable esters are those that are or can by hydrolysed, oxidised, metabolised, or otherwise converted, e.g., in plants, water, or soil, to the corresponding carboxylic acid which, depending upon the pH, may be in the dissociated or undissociated form. For example the ester includes esters derived from: $C_1$-$C_{12}$ alkyl alcohols, $C_3$-$C_{12}$ alkenyl alcohols, $C_3$-$C_{12}$ alkynyl alcohols or $C_7$-$C_{10}$ aryl-substituted alkyl alcohols. Examples of specific alcohols include, are not limited to: methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols.

Suitable esters can be prepared by techniques known in the art, this includes: the coupling an appropriate acid containing pesticide with an alcohol using an suitable activating agents, such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst; or by transesterification.

Examples of suitable salts include salts derived from alkali or alkaline earth metals and those derived from ammonia and amines Examples of appropriate cations include, but are not limited to: sodium, potassium and magnesium. Appropriate amine salts can include those derived from: ammonia, methylamine, dimethylamine, trimethylamine, isopropylamine, monoethanolamine, diethanolamine, triethanolamine, triisopropanolamine, 2-methylthiopropylamine, bisallylamine, 2-butoxyethylamine, morpholine, cyclododecylamine, tetraalkylammonium, choline or benzylamine.

Suitable salts can be prepared by treatment of an appropriate pesticide with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

In an embodiment, a formulation of the invention comprising a pesticide, such as 2-(2,4-dichlorophenoxy)acetic acid, does not form crystals after storage at 0° C. for seven days.

Other Components

Formulations of the invention can comprise other components such as carriers, safeners and/or dispersing agents.

In an embodiment, formulations of the invention comprise at least one acceptable carrier such as an agriculturally acceptable carrier. As the skilled person would understand, suitable carriers should not be phytotoxic to valuable crops, particularly at the concentrations employed in applying the formulations for selective weed control in the presence of crops, and should not react chemically with pesticide components or other formulation ingredients. Such mixtures can be designed for application directly to weeds or their locus or can be concentrates or formulations that are normally diluted with additional carriers before application. They can be solids, such as, for example, dusts, granules, water-dispersible granules, microcapsules or wettable powders, soluble powders or liquids, such as, for example, emulsifiable concentrates, solutions, emulsions or suspensions. The formulation can also be provided as a pre-mix or tank mixed. For example, the formulation can be an in-can formulation or a concentrate that is diluted (e.g., in a tank or a back pack) prior to application to an area that needs treating.

Suitable agricultural carriers include, but are not limited to, water, primary alcohols, secondary alcohols, tertiary alcohols, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate; tallow amine ethoxylates; PEG(400) dioleate-99.

Liquid carriers which can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrated formulations prior to application.

Suitable solid carriers include, but are not limited, to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

Dispersing agents are added to agrochemical formulations to facilitate dispersion and suspension during manufacture, and to ensure the particles redisperse into water, for example in a spray tank. Examples of dispersing agents include surfactants or surface active agents.

In some embodiments, the formulations of the invention further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes.

Surfactants which may also be used in the present formulations are described, inter alia, in McCutcheon's Detergents and Emulsifiers Annual, MC Publishing Corporation: Ridgewood, N.J., 1998 and in Encyclopaedia of Surfactants, Vol. I-III, Chemical Publishing Company: New York, 1980-81. Herein, a single surfactant or a blend of several surfactants can be used.

Nonionic surfactants are surfactants having no electrical charge when dissolved or dispersed in an aqueous medium. One or more nonionic surfactants may be used as they provide the desired wetting and emulsification actions and do not significantly inhibit spore stability and activity. The nonionic surfactant(s) may be either water soluble nonionic surfactants, water insoluble nonionic surfactants, or a combination of water soluble nonionic surfactants and water insoluble nonionic surfactants.

Non-limiting examples of water soluble nonionic surfactants include sorbitan fatty acid alcohol ethoxylates and sorbitan fatty acid ester ethoxylates. Commercially available water soluble nonionic surfactants may be suitable for the formulations described herein.

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty acid esters, sorbitol ethoxylate esters, or combinations thereof. Also included are EO/PO block copolymers (EO is ethylene oxide, PO is propylene oxide), EO polymers and copolymers, polyamines, and polyvinylpyrrolidones. Commercially available water insoluble nonionic surfactants may be suitable for the formulations described herein.

Anionic surfactants or mixtures of anionic and nonionic surfactants may also be used in formulating the compositions described herein. Anionic surfactants are surfactants having a hydrophilic moiety in an anionic or negatively charged state in aqueous solution. The formulations of the compositions described herein may comprise at least one anionic surfactant. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof. Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Formulations of the invention may comprise one or more polymeric surfactants. Suitable polymeric surfactants may include one or more nonionic polymeric surfactants, anionic polymeric surfactants, amphoteric polymeric surfactants, cationic polymeric surfactants, and combinations thereof.

Non-limiting examples of nonionic polymeric surfactants include polyalkylene oxide block copolymers, butyl block copolymers, nonionic block copolymers, acrylic copolymer solutions, nonionic random polymeric polymers, polyoxyethylene polyarl phenols, and nonionic polymeric dispersants. Commercially available nonionic polymeric surfactants may be suitable for the formulations described herein.

Non-limiting examples of anionic polymeric surfactants include styrene acrylic polymers, modified styrene acrylic polymers, and anionic polymeric dispersants. Commercially available anionic polymeric surfactants may be suitable for the formulations described herein.

Polymeric amphoteric surfactants suitable for formulating the compositions described herein include, but are not limited to, polymeric amphoteric dispersants. Commercially available polymeric amphoteric dispersants may be suitable for the formulations described herein.

Cationic polymeric surfactants suitable for formulating the compositions described herein include, but are not limited to, polyester/polyamine condensation polymers. Commercially available cationic polymeric surfactant may be suitable for the formulations described herein.

Non-limiting examples of low mole surfactants, which may also be referred to as low molar surfactants or low molecular weight surfactants, may include commercially available surfactants as available from Huntsman, Dow, Solvay Clariant, or Akzo Nobel, for example surfactants having $C_8$-20 linear or branched alkyl chains, low ethoxylated chain surfactants, nonophenyl and nonophenyl ethylates, alkylphenol ethoxylates, alkyl oxylates, and tallow amines Low mole surfactants include ionic and amphiphilic surfactants. Low molar surfactants include but are not limited to ethoxylated lauryl alcohol-3 and similar low mole ethoxylated alcohols, such as EO-3 to EO-6. Typically low mole surfactants are used as wetting agents.

In another embodiment, formulations of the compositions described herein may comprise organosilicone surfactants, silicone-based antifoams used as surfactants in silicone-based and mineral-oil based antifoams. In yet another embodiment, formulations of the compositions described herein may also comprise alkali metal salts of fatty acids (e.g., water soluble alkali metal salts of fatty acids and/or water insoluble alkali metal salts of fatty acids).

Other exemplary additives for use in formulations of the invention include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The formulations may also contain other compatible components, for example, other pesticides such as herbicides plant growth regulants, fungicides, insecticides, and the like and can be formulated with liquid fertilizers or solid, particulate fertilizer carriers such as ammonium nitrate, urea and the like.

In some embodiments, a formulation of the invention comprises one or more herbicide safeners, to enhance their selectivity. In some embodiments, the safeners are employed in rice, cereal, corn, or maize settings.

In some embodiments, the concentrated formulation is a clear, homogeneous liquid that is a stable formulation at temperatures in a range of about 0° C. to about 30° C. For example, the formulation may be a clear, homogeneous liquid which is stable at temperatures in a range of about 0° C. to about 30° C., for a period of at least 7 days, or at least 14 days, or at least 21 days. Furthermore the formulation may be a clear, homogeneous liquid which is stable at temperatures in a range of about 0° C. to about 30° C., for an extended period of time, for example, 1 year, or 2 years or 3 years. In some embodiments, the formulation is a concentrate which has reduced precipitation or does not exhibit crystallisation at temperatures of 0° C. or higher. In some embodiments, the formulation is a concentrate which has reduced or does not exhibit separation, precipitation, or crystallisation of active or any other components at low temperatures or over time. For example, the concentrate remains a clear solution at temperatures at or below about 0° C. (e.g., below −5° C., below −10° C., below −15° C.).

In some embodiments the formulation is stable at 0° C. for about 7, about 14 or about 21 days. Formulation stability may be measured at 7, 14 or 21 days, 1 year, 2 years or 3 years post formulation. In some embodiments the formulation has a shelf life of about 2 years. One method of testing shelf life of 2 years is accelerated testing at 54° C. for 14 days.

In some embodiments the formulation has a reduced hard water incompatibility and/or the resultant tank mix or dilution for use is clear or has reduced precipitation. In some embodiments it is clear, for example, for about 6 hours, or about 12 hours or about 24 hours after mixing. In some embodiments the formulation reduces sedimentation or precipitation after mixing with hard water.

Herein a formulation of the invention may comprise Compound 4:

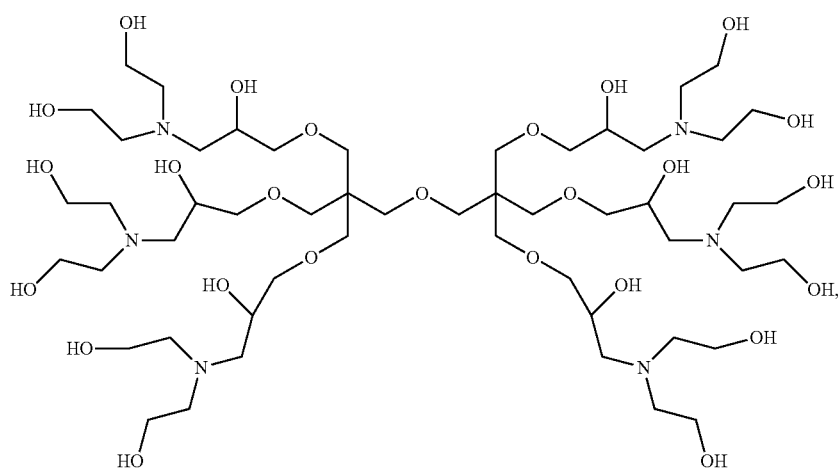

Compound 4 in an amount above about 0.1% and below about 40% (based on a w/w % of total formulation). For example, Compound 4 may be provided in an amount of at least about 0.1%, 0.25%, 5%, 0.75%, 1%, 2%, 3%, 4%, 5%, 6%, 7%, 8%, 9%, 10%, 15%, or 20% (based on a w/w % of total formulation). Compound 4 may be provided in an amount of less than about 40%, 35%, 30%, 25%, 20%, 15%, or 10% (based on a w/w % of total formulation). Compound 4 may be provided in a range between any two of these upper and lower amounts. In an embodiment, Compound 4 may be provided in a range of about 2% to about 10% (w/w) or about 6% to about 10%.

In one embodiment a formulation of the invention comprises a pesticide, such as a herbicide, and Compound 4:

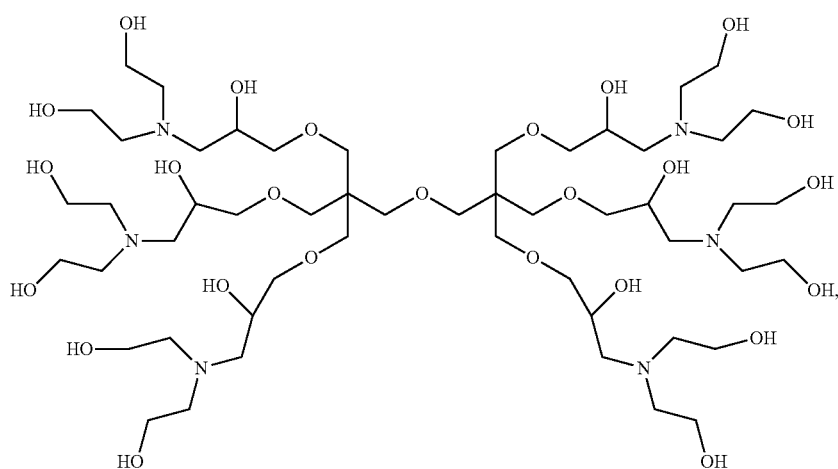

Compound 4 wherein the herbicide and Compound 4 are present in a w/w ratio of herbicide:Compound 4, of about 2000:1 to about 1:20, for example in a range of about 1000:1 to about 1:1, in a range of about 500:1 to about 1:1, or about 900:1 to about 10:1, about 500:1 to about 50:1 or about 625:1 to about 62.5 to 1.

In one embodiment a formulation of the invention comprises a phenoxyacetic acid, such as 2,4-D, or a salt or ester thereof, and Compound 4:

In another aspect, there may be provided a method of using or use of a dendrimer having the structure of Compound 4 in a formulation for facilitating at least one of dispersing the formulation into water, such as dispersing a concentrate formulation into water, stabilising the formulation or concentrated formulation. and enhancing wetting properties of the active.

The formulation may be an aqueous solution, such as an aqueous concentrate solution. The formulation may be a

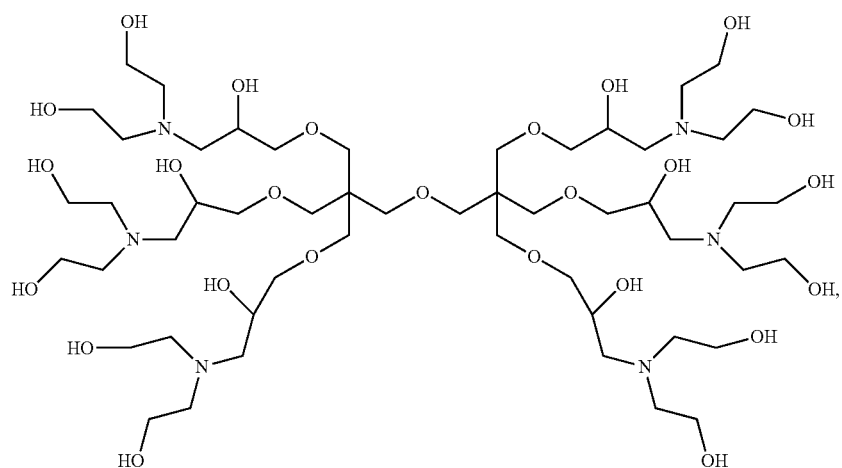

Compound 4 wherein the phenoxyacetic acid, such as 2,4-D, or a salt or ester thereof, and Compound 4 are present in a w/w ratio of phenoxyacetic acid:Compound 4, of about 10:1 to 800:1, for example in a range of about 20:1 to about 600:1, or in a range of about 50:1 to about 400:1. The w/w ratio of phenoxyacetic acid:Compound 4 may be in a range of about 625:1.4 to about 625:10.

In another aspect, there may be provided a method of using or use of the dendrimer having the structure of Compound 4 for improved solubilisation of a low mole surfactant in an aqueous solution. It will be appreciated that low mole surfactants may be provided by some of the surfactants as described herein. Low mole surfactants include ionic and amphiphilic surfactants. An example of a low mole surfactant is ethoxylated lauryl alcohol-3. In one embodiment, the dendrimer may be provided in an amount (w/w % of total formulation) in the range of about 1 to 30%, 2 to 25%, or 5 to 20%.

In another aspect, there may be provided a method of using or use of a dendrimer having the structure of Compound 4 for solubilisation of a hydrocarbon based oil in an aqueous solution. It will be appreciated that hydrocarbon based oils may be provided by some of the oils as described herein. An example of a hydrocarbon based oils is methylated seed oil. In one embodiment, the dendrimer may be provided in an amount (w/w % of total formulation) in the range of about 1 to 40%, 2 to 30%, or 5 to 25%.

In another aspect, there may be provided a method of using or use of a dendrimer having the structure of Compound 4 for reducing viscosity of a formulation. The formulation may be an aqueous solution. It will be appreciated that the formulation may include other components, for example pesticides as described herein, such as imidacloprid and other neonicotinoids and fungicides such tebaconozole and other azoles.

suspension concentrate (SC), soluble liquid (SL), oil in water emulsion (EW), or emulsifiable concentrate (EC). The formulation may comprise one or more carriers as described herein, for water, or primary, secondary or tertiary alcohols. The formulation may comprise one or more surfactants as described herein.

The suspension concentrate (SC) may be an aqueous suspension concentrate. It will be appreciated that a SC can provide a stable suspension of active constituent(s) with water as the fluid, which is intended for dilution with water before use. It will be appreciated that a soluble concentrate (SL) can provide a clear to opalescent liquid, which is to be applied as a solution of the active constituent after dilution in water. The liquid may contain water-insoluble formulants. It will be appreciated that a oil in water emulsion (EW) can provide a fluid, heterogeneous formulation comprising a solution of pesticide in an organic liquid dispersed as fine globules in a continuous water phase. It will be appreciated that a emulsifiable concentrate (EC) can provide a liquid, homogeneous formulation to be applied as an emulsion after dilution in water.

Uses

The use of a formulation of the invention will be dependent upon the active present therein.

In an embodiment, the formulation comprises a herbicide and is used for controlling weeds. Such formulations can be applied in any known technique for applying herbicides. Exemplary application techniques include, but are not limited to, spraying, atomizing, dusting, spreading, or direct application into water (in-water). The method of application can vary depending on the intended purpose.

In an embodiment, the formulation for use as a herbicide (neat or diluted) is applied to an area comprising, or which may comprise in the future, one or more undesirable plant species (weeds). Typically, the area will be a field but may be in a more confined space such as a garden or a greenhouse.

The formulations of the invention can be applied pre-emergence (before the emergence of undesirable vegetation) or post-emergence (i.e., during and/or after emergence of the undesirable vegetation). In some embodiments when the formulation is used in crops, the formulation can be applied after seeding or after the emergence of the crop plants. In some embodiments, the formulations of the invention shows good crop tolerance even when the crop has already emerged, and the formulations can be applied during or after the emergence of the crop plants. The formulations may be applied to seeds.

In some embodiments, the formulations of the invention are applied to vegetation or an area adjacent the vegetation or applying to soil or water to prevent the emergence or growth of vegetation by spraying (e.g., foliar spraying). In some embodiments, the spraying techniques use, for example, water as carrier and spray liquor rates of from about 0.5 litres per hectare (L/ha) to about 2000 L/ha or about 10 litres per hectare (L/ha) to about 2000 L/ha (e.g., from about 50 L/ha to about 1000 L/ha, or from about 100 to about 500 L/ha).

The formulations of the invention can be used to control undesired vegetation in a variety of crop and non-crop applications. In some embodiments, the formulations of the invention can be used for controlling undesired vegetation in crops or non-crop areas.

Herbicidal formulations of the invention are effective against a variety of types of undesirable vegetation. In some embodiments, the formulations of the invention can be used for controlling undesirable vegetation such as broadleaf weeds, woody plants, or semi-woody plants.

In an embodiment, the formulation comprises an insecticide and is used for controlling insects. The application of the formulation can be carried out both before and after the infection of the animals, plants, plant propagation materials, such as seeds, soil, surfaces, materials or rooms by the insects.

In one embodiment, the formulation comprising an insecticide is in the form of a bait which can be a liquid, a solid or a semisolid preparation (e.g. a gel).

In some embodiments, the formulation comprises a fungicide and is useful for controlling fungal infections.

Herein, the formulation concentration can range from about 5 g/L up to about 800 g/L or about 200 to about 600 g/L of active. In other embodiments dichlorophenoxy herbicide formulations, which are in the form of soluble liquids, can be formulated at about 400 g/L to about 800 g/L, or about 600 g/L to about 700 g/L, or about 625 g/L of active.

EXAMPLES

The closely related dendrimer Compound 1 [9-((3-(bis(2-hydroxyethyl)amino)-2-hydroxypropoxy) methyl)-9-ethyl-3,15-bis(2-hydroxyethyl)-7,11-dioxa-3,15-diazaheptadecane-1, 5,13,17-tetraol] was prepared using the procedure as outlined in WO2006/065266 A2.

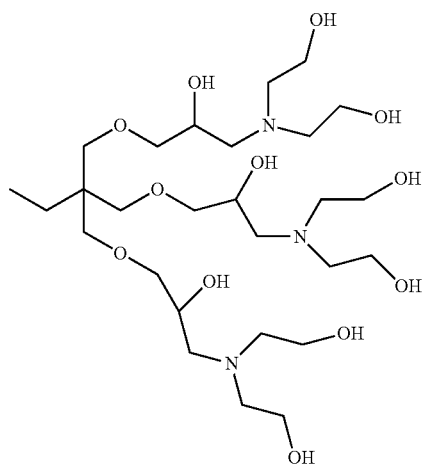

Compound 1

The closely related dendrimer Compound 8 [11-((3-(bis(2-methoxyethyl) amino)-2-hydroxypropoxy)methyl)-11-ethyl-5,17-bis(2-methoxyethyl)-2, 9,13,20-tetraoxa-5,17-diazahenicosane-7,15-diol] was prepared as outlined in WO2006/065266 A2.

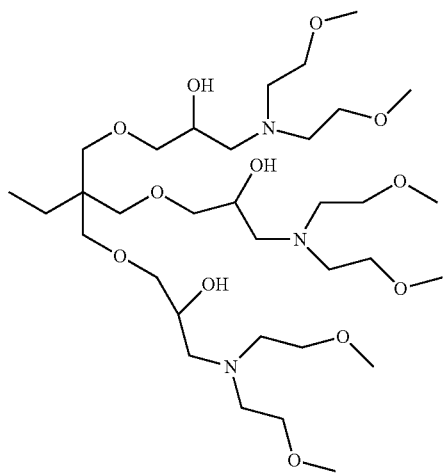

Compound 8

Compound 1 and Compound 8 are synthesised as comparative molecules and do not form part of the present invention.

Example 1—Synthesis of Dipentaerythritol-Epoxide

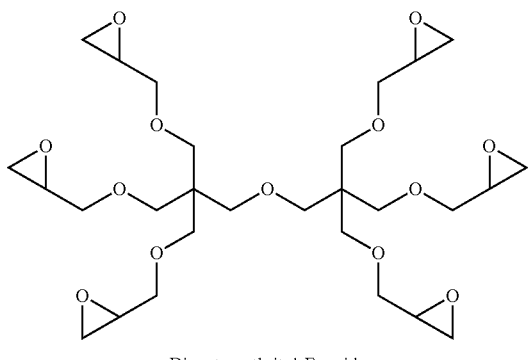

Dipentaerythritol-Epoxide

A stirred solution of dipentaerythritol (200 g, 0.78 mol) in DMSO (1.0 L) was prepared under an atmosphere of nitrogen at ambient temperature. To this was added powdered KOH (528 g, 9.4 mol) portion-wise, and the reaction mixture was left to stir for 2 hours at RT.

Epichlorohydrin (1351 g, 14.2 mol) was added dropwise over a period of 1-2 hours, maintaining reaction temperature at 20-25° C. The ensuing reaction mixture was left to stir for 24 hours. The contents were filtered over a bed of Hyflo filter aid (prepared in diethyl ether) and washed with ~2 litres of diethyl ether. The filtrate was washed with brine and then washed water and the total combined organic extracts dried over sodium sulphate. The solution was filtered and concentrated in vacuo to yield the thick brownish target intermediate Dipentaerythritol-Epoxide (320 g, 68.9%), ($^1$H-NMR (300 MHz, CDCl$_3$) δ (ppm) 2.53-2.64 (m, 6H); 2.72-2.82 (m, 6H); 3.06-3.18 (m, 6H); 3.25-3.59 (m, 24H) 3.6-3.79 (m, 4H). $^{13}$C-NMR (75 MHz, CDCl$_3$) δ (ppm) 43.6 (epoxide CH$_2$); 43.8 (C); 50.3 (epoxide CH); 71.6 (CH$_2$—O)).

Example 2—Synthesis of 9,9'-(oxybis(methylene)) bis(9-((3-(bis(2-hydroxyethyl) amino)-2-hydroxypropoxy)methyl)-3,15-bis(2-hydroxyethyl)-7,11-dioxa-3, 15-diazaheptadecane-1,5,13,17-tetraol) dendrimer (Compound 4)

To a stirred solution of Dipentaerythritol-Epoxide (100 g, 0.17 mol) in methanol (MeOH) (1000 mL) was added Diethanolamine (128 g, 1.12 mol). The ensuing reaction mixture was left to stir for 30 minutes then heated to reflux at 65° C. for 12 hours. The contents were allowed to cool then MeOH was removed by distillation in vacuo to yield a thick brownish semi solid target Compound 4 dendrimer (180 g, yield of 87.3%) was produced ($^1$H-NMR (300 MHz, CDCl$_3$) δ (ppm) 2.55-2.85 (m, 36H); 3.33-3.48 (m, 23H); 3.58-3.69 (m, 30H); 3.84-3.92 (m, 6H). $^{13}$C-NMR (75 MHz, CDCl$_3$) δ (ppm) 49.9 (C); 56.4 (CH$_2$); 59.2 (CH$_2$); 59.8 (CH$_2$); 68.0 (CH); 74.0 (CH$_2$)).

A mixture of dendrimers of Formula 1 are generated according to HPLC.

Example 3—2,4-D/Compound 4 Dendrimer—Hard Water Testing 342 ppm hard water was prepared as per CIPAC method MT18. The hard water was heated to 30° C. 98 ml of the heated hard water was combined with 2 ml of 2,4-D Amine (2,4-D 625 g/l Rygel, Adama Australia) and various % dendrimer as set out in the table below (the dendrimers are as described above) were added, and maintained at 30° C. for 24 hours following which the composition was observed for separation, sedimentation and general appearance. The results are provided as Table 1. All samples were clear at time of dilution and no samples showed separation or sedimentation.

TABLE 1

Clarity of hard water solutions comprising Dendrimer and 2,4-D.

| Dendrimer | Dendrimer % (w/w) | Diluent % (w/w) | Appearance at Addition | Appearance/ Sedimentation After 24 Hrs. |
|---|---|---|---|---|
| Standard (market) | — | | Clear | Clear |
| Compound-1 | 2 | | Clear | Hazy with sediment |
| Compound-1 | 5 | | Clear | Hazy with sediment |

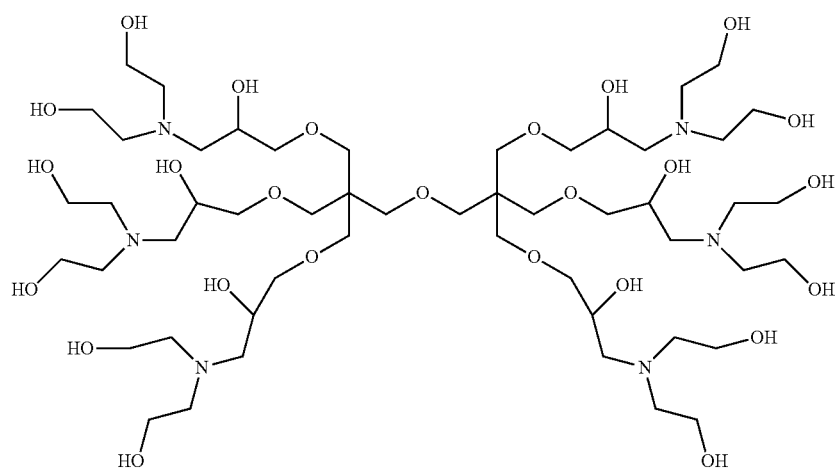

Compound 4

TABLE 1-continued

Clarity of hard water solutions comprising Dendrimer and 2,4-D.

| Dendrimer | Dendrimer % (w/w) | Diluent % (w/w) | Appearance at Addition | Appearance/ Sedimentation After 24 Hrs. |
|---|---|---|---|---|
| Compound-1 | 10 | | Clear | Hazy with sediment |
| Compound-1 | 1.4 | 0.6% DEG | Clear | Hazy with sediment |
| Compound-1 | 3.5 | 1.5% DEG | Clear | Hazy with sediment |
| Compound-1 | 7 | 3% DEG | Clear | Hazy with sediment |
| Compound-4 | 2 | | Clear | Clear |
| Compound-4 | 5 | | Clear | Clear |
| Compound-4 | 10 | | Clear | Clear |
| Compound-4 | 1.4 | 0.6% DEG | Clear | Clear |

TABLE 1-continued

Clarity of hard water solutions comprising Dendrimer and 2,4-D.

| Dendrimer | Dendrimer % (w/w) | Diluent % (w/w) | Appearance at Addition (Addition to 342 ppm HW water at 30° C.) | Appearance/Sedimentation After 24 Hrs. (Addition to 342 ppm HW water at 30° C.) |
|---|---|---|---|---|
| Compound-4 | 3.5 | 1.5% DEG | Clear | Clear |
| Compound-4 | 7 | 3% DEG | Clear | Clear |
| Compound-8 | 2 | | Clear | Hazy with sediment |
| Compound-8 | 5 | | Clear | Hazy with sediment | freezer and observations were captured for any liquid separation and solid crystallisation. In a related experiment, formulations were prepared with seeding with 2,4-D Amine salt (Shanghai Biochemical Sci. Ltd., purity 98 in order to hasten rate of crystallisation. The results are provided in Table 2.

In the experiment without seeding, the market sample and 2 and 5% of Compound 1 resulted in crystallisation, whereas the use of compound 4 at all levels tested did not result in crystallisation. Compound 4 was more effective than compound 1, particularly below 10%.

Similarly, with seeding, samples with Compound 1 crystallised at all the dosages, whereas samples with Compound 4 remained stable with 7 and 10% dendrimer. In the experiment where the likelihood of crystallisation was greater, Compound 4 was more effective than compound 1 above 5%, and in particular at 7%.

TABLE 2

Crystallisation of solutions comprising dendrimers and 2,4D

| Dendrimer | Dendrimer % | Diethylene Glycol % | Crystallisation After 14 Days at 0° C. | Crystallisation After 7 Days at 0° C. | Crystallisation After 7 Days at 0° C. With Seeding |
|---|---|---|---|---|---|
| Control (2,4-D Market Sample) | 0 | 0 | Crystallised | Crystallised | — |
| Compound 1 | 1.4 | 0.6 | Crystallised | — | Crystallised |
|  | 2 |  | Crystallised | Crystallised | — |
|  | 3.5 | 1.5 | Crystallised | — | Crystallised |
|  | 5 |  | Crystallised | Crystallised | — |
|  | 7 | 3 | Crystallised | — | Crystallised |
|  | 10 |  | Crystallised | No | — |
| Compound 4 | 1.4 | 0.6 | Crystallised | — | Crystallised |
|  | 2 |  | Crystallised | No | Crystallised |
|  | 3.5 | 1.5 | No | — | Crystallised |
|  | 5 |  | Crystallised | No | Crystallised |
|  | 7 | 3 | No | — | No, Clear |
|  | 10 |  | No | No | No, Clear |
| No dendrimer | — | 0.6 | No | No | — |
|  | — | 1.5 | Crystallised | No | — |
|  | — | 3 | Crystallised | Crystallised | — |

TABLE 1-continued

Clarity of hard water solutions comprising Dendrimer and 2,4-D.

| Dendrimer | Dendrimer % (w/w) | Diluent % (w/w) | Appearance at Addition (Addition to 342 ppm HW water at 30° C.) | Appearance/Sedimentation After 24 Hrs. (Addition to 342 ppm HW water at 30° C.) |
|---|---|---|---|---|
| Compound-8 | 10 | | Clear | Hazy with sediment |
| — | | 2% water | Clear | Clear |
| — | | 5% water | Clear | Clear |
| — | | 10% water | Clear | Clear |

Compound 4 produced clear 2,4-D solutions at all concentrations tested (from 1.4 to 10%) in hard water, whereas the closely related Compounds 1 and 8 resulted in hazy solutions with sediment.

Example 4—2'4 D/Compound 4 Formulation Stability Study 20 ml of 2,4-D Amine(2,4-D 625 g/l market sample, Rygel, Adama Australia) was transferred to 25 ml clear vials and dendrimer added (with or without 30% Dithethylene Glycol). Caps were tightened to ensure no moisture entered the vials. Formulations were placed in a freezer at 0° C. After 7-days at 0° C., formulations were taken out of the Example 5—Solubilization of Water Insoluble Surfactant: Ethoxylated Lauryl Alcohol-3 M (Low Molar Surfactant)

5% w/w aqueous solution of Ethoxylated Lauryl alcohol-9 mole (water soluble surfactant) was prepared in Deionized water (2.5 g in 47.5 ml). Dendrimer compounds 1 and 4 were diluted 70:30 w/w in Diethylene glycol. The 5% Ethoxylated Lauryl alcohol-9 M (LA-9) solution was combined with dendrimer DEG solution at 90:10, 80:20 and 70:30 w/w (total weight 50 g).

Ethoxylated lauryl alcohol-3 mole (water insoluble surfactant) was added dropwise, while stirring, to the 50 g LA-9 solution (with or without dendrimer), until it became hazy. The weight of Ethoxylated lauryl alcohol-3 M added was recorded.

Inclusion of Compound 4 enabled better solubilisation of low molar surfactant, Ethoxylated lauryl alcohol-3 M. Compound 4 increased solubilisation by 72% over LA-9 without dendrimer. Such low molar surfactants can be used for suspension concentrate (SC), soluble concentrate (SL), oil in water emulsion (EW) and emulsifiable concentrate (EC) formulations.

TABLE 3

Solubilization of Ethoxylated Lauryl alcohol-3M

Quantity LA-3 added (g) to LA-9 solution
(with and without dendrimer).
Ratio LA-9 solution:dendrimer/DEG solution (w/w)

|  | 100:0 | 90:10 | 80:20 | 70:30 |
|---|---|---|---|---|
| % dendrimer (w/w) | 0% | 7% | 14% | 21% |
| Compound 1 | 1.67 | 1.83 | 2.00 | 1.96 |
| Compound 4 | 1.67 | 2.11 | 2.86 | 2.01 |
| No dendrimer | 1.67 | ND | 1.91 | ND |

Example 6—Solubilization of Methylated Seed Oil (MSO) (Water Insoluble Oil) in Aqueous Solution of Ethoxylated Lauryl Alcohol-9 M 10% aqueous solution of Ethoxylated Lauryl alcohol-9 mole (water soluble surfactant) was prepared in Deionized water (5 g in 45 ml). Dendrimer compounds 1 and 4 were prepared 70:30 w/w in Diethylene glycol (DEG). The 10% Ethoxylated Lauryl alcohol-9 M (LA-9) solution was combined with dendrimer DEG solution at 80:20 and 60:40 w/w (total weight of 50 g).

Methylated seed oil (MSO) (STEPOSOL-ROE-W, canola oil methyl ester, Stepan) was added dropwise under stirring to the 10% LA-9 solution (with or without dendimers), until the solution became hazy. Weight of MSO added was recorded.

Compound 4 increased solubilisation of water insoluble oil, Methylated seed oil in aqueous solution by 110%.

TABLE 4

Solubilization of Methylated seed oil

Quantity MSO added (g) to 10% LA-9 solution
(with or without dendrimer)
Ratio LA-9 solution:dendrimer/DEG solution (w/w)

|  | 100:0 | 80:20 | 60:40 |
|---|---|---|---|
| % dendrimer (w/w) | 0% | 14% | 28% |
| Compound 1 | 0.44 | 0.54 | 0.56 |
| Compound 4 | 0.44 | 0.92 | 0.81 |

Example 7—Cloud Point Studies 1 gm. of dendrimer solution (70:30 w/w dendrimer [Compound 1 or Compound 4]:Diethylene Glycol) was dissolved in 99 gm. of 10% NaOH solution in Deionized water and heated until hazy. Temperature of the solution was measured using calibrated thermometer.

The solution containing Compound-1 turned to hazy at 65° C. whereas the solution containing Compound-4 remained clear at greater than 80° C. This showed the improved formulation characteristics of Compound-4 in water as compared to Compound-1. Cloud point is an important indicator of solubility of the compound and related to storage stability, and in particular phase separation and instability.

Example 8—Water Value of Dendrimers with Solvent 50 g Aqueous solution of Dendrimer were prepared containing 7% dendrimer and 3% Diethylene glycol (DEG) by weight. Solvesso 200 (C10-13 aromatic hydrocarbon solvent) was added dropwise under stirring until the solution became hazy. Weight of Solvesso added was recorded.

The maximum increase in solubilisation of the Solvesso in aqueous solution was achieved with Compound 4.

TABLE 5

Solubilization of Solvent

| | Quantity Solvesso 200 added (g) |
|---|---|
| No dendrimer | 0 |
| Compound 1 | 1.31 |
| Compound 4 | 2.15 |

Solvesso 200 is insoluble in water. Dendimer 4 was able to incorporate this organic solvent into aqueous solution, suitable for EC and EW formulations.

Example 9—Dynamic Viscosity 50 g aqueous solution of dendrimer (7% dendrimer and 3% DEG) was prepared in deionized water in a beaker, and subjected to dynamic viscosity measurement using Brookfield viscometer at ambient temperature. Viscosity studies were conducted using spindle no. 63 at 50 rpm. It was observed that viscosity of Compound-1 solution was 1.8 cps and Compound-4 solution was 0.6 cps.

Example 10—Tebuconazole 600 SC/Compound 4 Dendrimer—Hard Water Testing

Tebuconazole 600 SC Formulation

Formulations were prepared by mixing water, surfactant, dispersing agent, wetting agent and antifoam together then gradually adding active. High shear mix for 20-30 minutes to disperse formulation ingredients in water before adding the active and mixing until homogeneous. The mixture was milled on a Dyno bead mill (1 m/s) with 0.4-0.6 mm beads at max. 40° C. until particle size was <4 um. Dendrimer compound (in DEG) was added and stirred for 20 minutes. Thickener and antimicrobial was then added and stirred for 20 minutes. Formulations were deaerated by sonication.

TABLE 6

Milled mixture

| | Function | g |
|---|---|---|
| tebuconazole tech (97.4%) | | 56 |
| Propylene glycol | humectant | 2.5 |
| Rhodasurf 860P | Surfactant | 0.7 |
| Soprophor TSP/461 | Dispersing | 2.7 |
| Geronol CF/AR | Surfactant | 4.7 |
| Gensil 2030 | Antifoam | 0.09 |
| Water | | 28.29 |

TABLE 7

Post milling additions

| | Control (g) | dendrimer containing formulation (g) |
|---|---|---|
| Dendrimer | 0 | 0.7 |
| DEG | 0 | 0.3 |
| Rhodapol 23 (Thickener) | 0.08 | 0.08 |

TABLE 7-continued

Post milling additions

|  | Control (g) | dendrimer containing formulation (g) |
|---|---|---|
| Water (thickener diluent) | 3.92 | 3.92 |
| Glokill 77 (antimicrobial) | 0.02 | 0.02 |

98 ml of 342 ppm hard water (prepared as per CIPAC method MT18) was heated to 30° C. before adding 2 ml. of Tebuconazole 600 SC formulation. Temperature was maintained at 30° C. for 24 hours and formulation characteristics were studied for suspension stability, wetting, column thinning/separation and sedimentation.

Wetting studies were conducted by placing one drop of Tebuconazole 600 SC formulation in 342 ppm hard water at 30° C. and recording the time when all the formulation particles were wet and dispersed in water.

TABLE 8

Tebuconazole 600 SC formulation characteristics

| Tebuconazole 600 SC Formulation | Dendrimer (%) | Viscosity RT | Viscosity 0 C. | Viscosity 54 C. | Wetting (Sec.) | Suspensibility (Sediment) Column Thinning | Suspensibility (Sediment) Sediment (ml.) |
|---|---|---|---|---|---|---|---|
| Standard (without dendrimer) | 0 | 970 | 1035 | 1130 | 29 | 20 ml. Top thinning | 0.5/ Compact |
| Compound-1 | 0.7 | 720 | 786 | 743 | 33.3 | 10 ml. Top thinning | 0.5/ Compact |
| Compond-4 | 0.7 | 730 | 744 | 730 | 9.9 | No Thinning | <0.5/ Compact |

Additional formulations were developed, and formulation characteristics were studied for suspension stability, and viscosity.

TABLE 9

Viscosity observations

|  | Observation | Viscosity (cP) 0 C. | Viscosity (cP) RT |
|---|---|---|---|
| Control: (No dendrimer) 0.8% DS10025- (organo-silicone super spreader) | Dense, medium sediment at 0 C. and RT | 1038 | 945 |
| 0.8% Compound 1 | Pseudoplastic liquid, no sediment at 0 C. and RT | 2844 | 2566 |
| 0.8% Compound 4 | No sediment at 0 C., fluffy, low sediment at RT | 514 | 672 |

Compound 4 showed reduced wetting time, stable formulation and reduced viscosity.

Example 11—Imidacloprid 700SC Formulations with Reduced Viscosity

Imidacloprid formulations were prepared by using high shear mixing to disperse formulation ingredients in 75% of the required water before adding the active and mixing until homogeneous. The mixture was milled on a bead mill (4 m/s) at 30-35° C. for 1 complete pass. Thickener, glycerine and residual water were then added under high shear mixing.

TABLE 10

Imidacloprid Formulation

|  | g/L |
|---|---|
| Imidacloprid tech (97%) | 721.65 |
| Atlox 4913 | 70 |
| Terspese 4894 | 20 |
| Gensil 2030 | 4.8 |
| Glycerine | 100 |
| Glokill 77 | 0.85 |
| active gel 53 | 1.05 |
| Supragil MNS/25 | 5 |
| Dendrimer compound (or water as control) | 20 |
| Water | 285.85 |
| Glycerine | 25 |
| Cellulon PX (1%)- thickener | 0.25 |
| Total | 1245 |

Formulations were tested for viscosity (using a Brookfield LV viscometer) low temperature stability (0 C for 7 days) and RT stability. Many other dendrimers containing formulations prepared either solidified on milling or pre-milling Compound 4 reduced viscosity and provided greater formulation stability.

TABLE 11

700 g/L Formulation characteristics

|  | Observation | Viscosity (cP) 0 C. | Viscosity (cP) RT |
|---|---|---|---|
| No dendrimer | Dense, medium sediment at 0 C. and RT | 1500 | 3000 |
| Compound 4 (2-OH) | No sediment at 0 C., fluffy, low sediment at RT | 552 | 574 |

Low sedimentation is less than 5% of total volume. Medium sedimentation is 5-30% of total volume.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The invention claimed is:
1. A dendrimer having the structure of Compound 4:

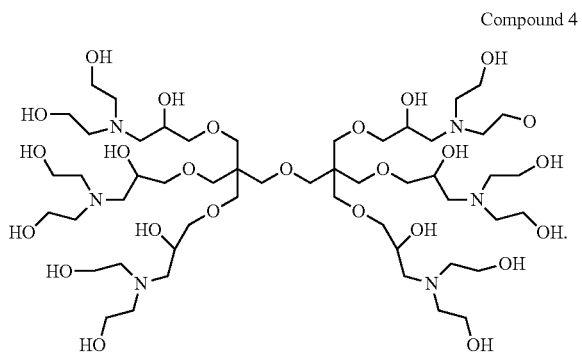 [SMILES: OCCN(CCO)CC(O)COCC(COCC(O)CN(CCO)CCO)(COCC(O)CN(CCO)CCO)COCC(COCC(O)CN(CCO)CCO)(COCC(O)CN(CCO)CCO)COCC(O)CN(CCO)CCO]

Compound 4

2. A formulation comprising a dendrimer having the structure of Compound 4

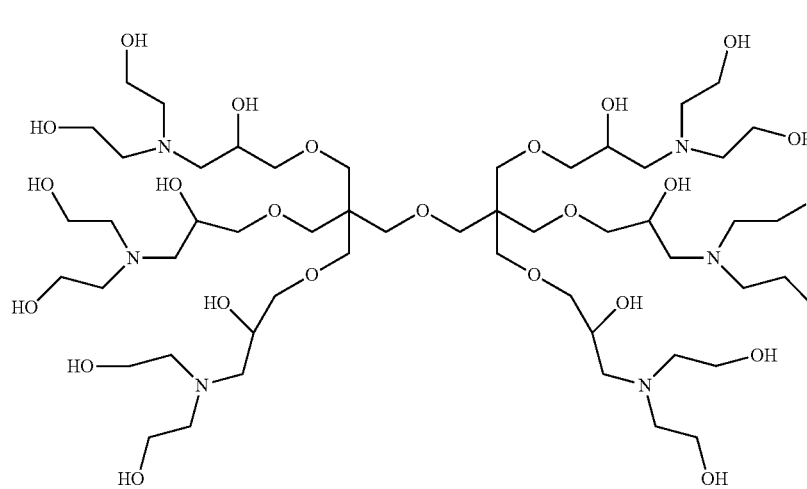

Compound 4 and one or more acceptable carriers.
3. The formulation of claim 2, which further comprises a pesticide.
4. The formulation of claim 3, wherein the pesticide is selected from: a phenoxy herbicide, a dichloro-benzoic acid herbicide, a trichloro-benzoic acid herbicide, an imidazolinone herbicide, a neonicotinoid insecticide and an organophosphate insecticide.
5. The formulation of claim 3, wherein the pesticide is selected from: a phenoxy herbicide, a dichloro-benzoic acid herbicide and a trichloro-benzoic acid herbicide.
6. The formulation of claim 4, wherein the phenoxy herbicide is a mono- or di-chlorophenoxy herbicide.
7. The formulation of claim 4, wherein the phenoxy herbicide is a phenoxyacetic herbicide.
8. The formulation of claim 7, wherein phenoxyacetic herbicide is selected from: 2-(2,4-dichlorophenoxy)acetic acid (2,4-D), 2-(4-chlorophenoxy)acetic acid, 1-(dimethoxyphosphinyl) ethyl 2-(2,4-dichlorophenoxy)acetate, 2-(3,4-dichlorophenoxy) acetic acid, 2-(4-chloro-2-methylphenoxy)acetic acid, S-ethyl 2-(4-chloro-2-methylphenoxy) ethanethioate and 2-(2,4,5-trichlorophenoxy)acetic acid, or salts and esters thereof.
9. The formulation of claim 5, wherein the dichlorobenzoic acid herbicide or trichloro-benzoic acid herbicide is selected from: (phenylimino)di-2,1-ethanediyl bis(3,6-dichloro-2-methoxybenzoate), 3-amino-2,5-dichlorobenzoic acid, 3,6-dichloro-2-methoxybenzoic acid, 2,3,6-trichlorobenzoic acid and 2,3,5-trichloro-6-methoxybenzoic acid, or salts and esters thereof.
10. The formulation of claim 2 wherein the formulation is a soluble liquid formulation.
11. The formulation of claim 2, wherein the formulation is an aqueous solution.
12. The formulation of claim 2, wherein the formulation is a suspension concentrate (SC), soluble concentrate (SL), oil in water emulsion (EW), or emulsifiable concentrate (EC).
13. The formulation of claim 2, wherein the carrier is selected from the group consisting of: water, primary alcohols, secondary alcohols, and tertiary alcohols.
14. The formulation of claim 2, further comprising a surfactant.
15. The formulation of claim 14, wherein the surfactant is a non-ionic or cationic surfactant.
16. The formulation of claim 14, wherein the surfactant is an amine based surfactant.
17. The formulation of claim 14, wherein the surfactant is selected from the group consisting of: surfactants having C8-20 linear or branched alkyl chains, ethoxylated chain surfactants wherein the degree of ethoxylation is from 3 to 6, alkylphenol ethoxylates, alkyloxylates, and tallow amines.
18. The formulation of claim 2, wherein Compound 4 is at a concentration in a range of 5% to 20% (w/w).
19. A method of controlling a pest in an area, the method comprising applying to the area a formulation comprising a dendrimer having the structure:

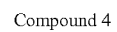
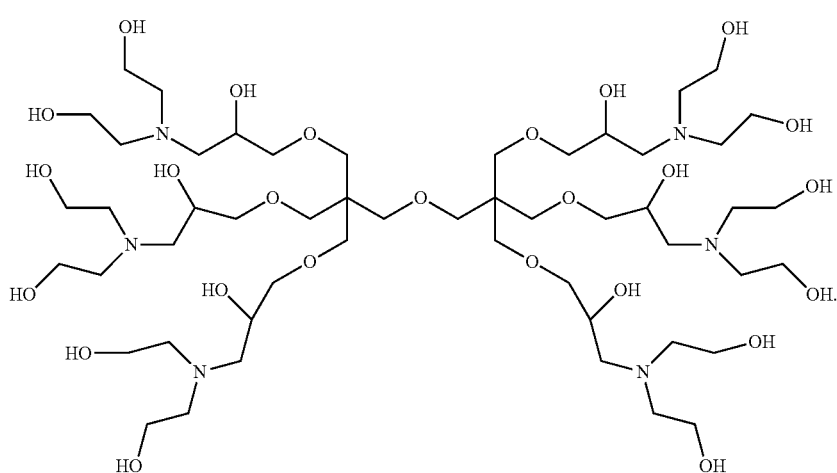
and a phenoxy herbicide.
20. The method of claim 19, wherein the pest is a weed.
\* \* \* \* \*